United States Patent
Hou et al.

(10) Patent No.: US 11,150,166 B2
(45) Date of Patent: Oct. 19, 2021

(54) METHOD FOR SAMPLING GROUNDWATER

(71) Applicant: Tsinghua University, Beijing (CN)

(72) Inventors: De-Yi Hou, Beijing (CN); Yi-Dong Wang, Beijing (CN); Guang-He Li, Beijing (CN); Xu Zhang, Beijing (CN); Fang Zhang, Beijing (CN)

(73) Assignee: TSINGHUA UNIVERSITY, Beijing (CN)

( * ) Notice: Subject to any disclaimer, the term of this patent is extended or adjusted under 35 U.S.C. 154(b) by 25 days.

(21) Appl. No.: 16/805,833

(22) Filed: Mar. 2, 2020

(65) Prior Publication Data

US 2020/0284697 A1 Sep. 10, 2020

(30) Foreign Application Priority Data

Mar. 7, 2019 (CN) .......................... 201910170822.7

(51) Int. Cl.
*G01N 1/14* (2006.01)
*G01N 33/18* (2006.01)
*G01F 23/00* (2006.01)

(52) U.S. Cl.
CPC ............. *G01N 1/14* (2013.01); *G01F 23/00* (2013.01); *G01N 33/18* (2013.01)

(58) Field of Classification Search
CPC ... E02D 1/06; G01N 1/14; G01N 1/12; G01N 33/1826; G01N 1/10; G01N 33/18
See application file for complete search history.

(56) References Cited

U.S. PATENT DOCUMENTS

| | | | | |
|---|---|---|---|---|
| 4,727,936 A | * | 3/1988 | Mioduszewski | E21B 43/129 166/105 |
| 5,147,185 A | * | 9/1992 | Niehaus | E21B 43/121 417/394 |
| 5,238,060 A | * | 8/1993 | Niehaus | E21B 43/121 166/68 |
| 5,271,467 A | * | 12/1993 | Lynch | B09C 1/002 166/105 |

(Continued)

FOREIGN PATENT DOCUMENTS

| | | |
|---|---|---|
| CN | 102410977 | 4/2012 |
| CN | 102507264 | 6/2012 |

(Continued)

OTHER PUBLICATIONS

International Search Report of PCT/CN2019/120818.
(Continued)

*Primary Examiner* — David A. Rogers

(57) ABSTRACT

The disclosure provides a method for sampling groundwater. The method includes extracting groundwater from a monitoring well in a first flow rate; monitoring groundwater level in real-time, and calculating a decrease of the groundwater level during the extracting in the first flow rate based on the real-time monitored groundwater level; when the decrease of the groundwater level is equal to a first value, extracting groundwater from the monitoring well in a second flow rate, the second flow rate being smaller than the first flow rate; and when the groundwater level is in an equilibration state, extracting groundwater from the monitoring well and using the extracted groundwater at this time as a representative groundwater.

11 Claims, 3 Drawing Sheets

(56) References Cited

U.S. PATENT DOCUMENTS

| | | | | |
|---|---|---|---|---|
| RE34,754 E * | 10/1994 | Dickinson | ............. | E21B 43/129 166/105 |
| 5,606,138 A * | 2/1997 | Saarenketo | ............. | G01N 1/14 73/864.34 |
| 5,611,671 A * | 3/1997 | Tripp, Jr. | ............. | E21B 43/121 417/118 |
| 6,306,350 B1 | 10/2001 | Mereish | ............. | G01N 1/14 210/445 |
| 6,491,828 B1 * | 12/2002 | Sivavec | ............. | B09C 1/00 166/167 |
| 6,547,004 B2 * | 4/2003 | Last | ............. | E21B 49/081 166/250.03 |
| 9,606,028 B2 * | 3/2017 | Detweiller | ............. | G01S 15/86 |
| 10,591,389 B2 * | 3/2020 | Trumbo | ............. | G01N 33/1826 |
| 11,002,643 B1 * | 5/2021 | Ulrich | ............. | E21B 43/084 |
| 11,060,956 B2 * | 7/2021 | Trumbo | ............. | G01N 33/1833 |
| 2002/0157825 A1 * | 10/2002 | Learned | ............. | E21B 49/08 166/264 |
| 2002/0166663 A1 | 11/2002 | Last et al. | | |
| 2004/0091378 A1 * | 5/2004 | McCall | ............. | F04B 43/084 417/472 |
| 2007/0221573 A2 * | 9/2007 | Mailath | ............. | B09C 1/002 210/610 |
| 2008/0236257 A1 * | 10/2008 | de Jonge | ............. | E21B 49/08 73/61.59 |
| 2009/0123340 A1 * | 5/2009 | Knudsen | ............. | G08B 21/12 422/105 |
| 2010/0212406 A1 * | 8/2010 | Browne | ............. | B01D 19/0036 73/61.41 |
| 2011/0003400 A1 * | 1/2011 | Halden | ............. | G01N 1/10 436/501 |
| 2013/0145867 A1 * | 6/2013 | Michelin | ............. | G01N 1/14 73/863.01 |
| 2015/0233884 A1 * | 8/2015 | Burge | ............. | E02D 1/06 204/416 |
| 2016/0033462 A1 * | 2/2016 | Singer | ............. | G01N 33/0047 702/6 |
| 2016/0348482 A1 * | 12/2016 | Keller | ............. | E21B 49/084 |
| 2019/0271615 A1 * | 9/2019 | Trumbo | ............. | G01N 1/14 |
| 2020/0072709 A1 * | 3/2020 | Garcia | ............. | G01N 1/4077 |
| 2020/0088609 A1 * | 3/2020 | Beck | ............. | G01N 33/18 |
| 2020/0240878 A1 * | 7/2020 | Trumbo | ............. | G01N 33/1833 |

FOREIGN PATENT DOCUMENTS

| | | |
|---|---|---|
| CN | 202330235 | 7/2012 |
| CN | 104406819 | 3/2015 |
| CN | 104832170 | 8/2015 |
| CN | 206330786 | 7/2017 |
| CN | 208223899 | 12/2018 |
| CN | 208459072 | 2/2019 |
| JP | 2007147322 | 6/2007 |
| KR | 10120544 | 11/2012 |

OTHER PUBLICATIONS

Yang Qing et al: "Monitoring Technique and Management Strategy of Groundwater Pollution Caused by Gas Station Leakage" «China Environmental Press» , pp. 85-86.

Li Hai-ying et al: "Discussion on Influence of Groundwater Sampling Method to Analysis Results", «Guangzhou Chemical Industry» , vol. 44, No. 20, Oct. 31, 2016, pp. 121-122,164.

Li Wenpan et al.: "Comparative Study of Sampling Methods in Ground Water" , «Environmental Monitoring in China» , vol. 32, No. 4, Aug. 31, 2016, pp. 104-108.

* cited by examiner

METHOD FOR SAMPLING GROUNDWATER

CROSS-REFERENCE TO RELATED APPLICATIONS

This application claims all benefits accruing under 35 U.S.C. § 119 from China Patent Application No. 201910170822.7, filed on Mar. 7, 2019, in the China National Intellectual Property Administration, the content of which are hereby incorporated by reference in their entirety.

FIELD

The application relates to the technical field of environmental monitoring, and in particular, to methods for sampling groundwater.

BACKGROUND

With the economic development and social progress, the size of cities is getting larger and larger. In groundwater treatment and remediation, accurate monitoring of groundwater quality is essential for polluted site investigation, environmental risk management, and performance assessment of restoration systems. Groundwater quality may be affected by complex factors such as the soil matrix introduced from the well drilling. In addition, groundwater remaining in the monitoring well for a period of time may not accurately reflect the groundwater quality of the local area. For example, the volatile organic compounds (VOC) concentration of groundwater in the well may decrease as the VOC volatilizing out from the well. Besides, oxygen gas in the air may diffuse into groundwater, and oxidize substances in groundwater, such as sulfides and ferrous ions. Therefore, representative groundwater samples are needed to be obtained and monitored to accurately monitor the groundwater quality.

SUMMARY

What is needed, therefore, is to provide a method for sampling representative groundwater.

In an embodiment of the method for sampling groundwater, groundwater is extracted from a monitoring well at a first flow rate. The groundwater level is monitored in real-time. A decrease of the groundwater level during the extraction at the first flow rate is calculated based on the real-time monitored groundwater level. When the decrease of the groundwater level is equal to a first value, the extraction flow rate of groundwater is changed from the first flow rate to a second flow rate. The second flow rate is smaller than the first flow rate. When the groundwater level is in an equilibration state, groundwater is extracted from the monitoring well and used as a representative groundwater.

One or more embodiments of the disclosure are set forth in the drawings and the detailed description. Other features, objects, and advantages of the disclosure will become more apparent from the detailed description, the drawings, and the claims.

BRIEF DESCRIPTION OF THE DRAWINGS

Implementations will now be described, by way of example only, with reference to the attached figures.

DETAILED DESCRIPTION

In order to make the objectives, features and advantages of the present disclosure more comprehensible, the exemplified embodiments of the present disclosure will be illustrated in detail below with reference to the drawings. Many details are described in the following description, in order to understand the present disclosure thoroughly. However, the disclosure can be implemented in many other ways other than the ways described herein. Those skilled in the art can make some similar improvements without departing from the spirit of the present disclosure. Therefore, the present disclosure is not limited to the exemplified embodiments described below.

Figure 1:
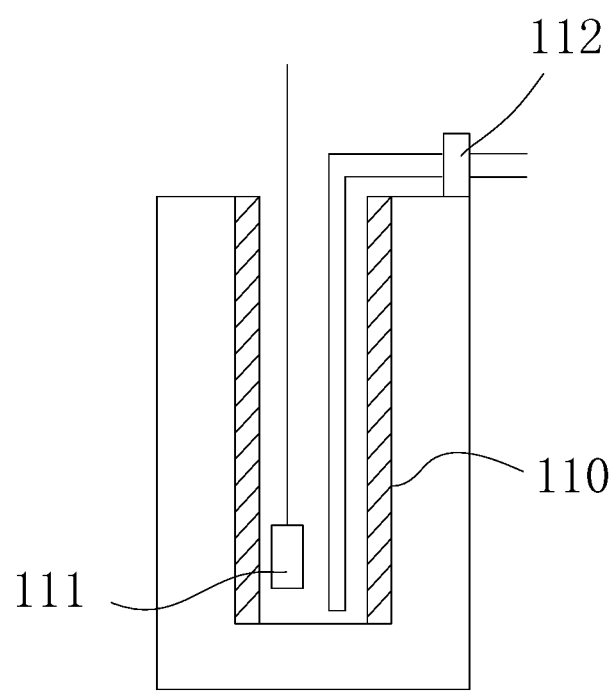
FIG. 1 is a schematic structural view of an embodiment of a groundwater sampling system.

Referring to FIG. 1, in an embodiment, a method for sampling groundwater can be applied in a groundwater sampling system. An embodiment of the groundwater sampling system includes a monitoring well 110, a water level indicator 111, and a water suction pump 112.

The monitoring well 110 extends from the ground surface to an underground area to be monitored. At least a section of the sidewall of the monitoring well 110 is a water permeable wall that is capable of having groundwater permeated from soil into the monitoring well 110. The water permeable wall can be made of gravel sandwiched between screens. In an embodiment, the sidewall of the monitoring well 110 is divided into three sections, the upper section, the middle section, and the lower section. The upper section of the sidewall adjacent to the opening of the monitoring well 110 can be made of cement, which is not water permeable. The lower section of the sidewall adjacent to the bottom of the monitoring well 110 can be the water permeable wall made of gravel and screens. The middle section of the sidewall can be made of bentonite, to join the upper and lower sections.

The water level indicator 111 is disposed in the monitoring well 110, and can measure and monitor the groundwater level in the monitoring well 110 in real-time. The groundwater level is the height of the groundwater surface relative to a fixed elevation point, such as the bottom of the monitoring well 110. In an embodiment, the water level indicator 111 is electrically connected to the water suction pump 112, and transmits real-time data of the groundwater level to the water suction pump 112.

The water suction pump 112 can pump groundwater out from the monitoring well 110, and can continuously adjust a extracting flow rate thereof. In an embodiment, the extracting flow rate of the water suction pump 112 can be adjusted in a range from about 0.3 L/min to about 3 L/min. Thereby, the water suction pump 112 is capable of extracting groundwater out from the monitoring well 110 at a variable flow rate. In an embodiment, a controller of the monitoring well 110 is capable of real-time receiving the data of the groundwater level send from the water level indicator 111, calculating the decrease of the groundwater level in the monitoring well 110 during the groundwater extraction based on the received data, and varying the extracting flow rate according to the groundwater level decrease.

The specific types and forms of the water level indicator 111 and the water suction pump 112 are not limited. The water suction pump 112 can be such as peristaltic pump, centrifugal pump, airbag pump, or submersible pump.

In the beginning of extracting groundwater by the water suction pump 112, a relatively large flow rate can be used to rapidly decrease the groundwater level in the monitoring well 110. Meanwhile, the representative groundwater in soil outside the monitoring well 110 can enter the monitoring well 110 through the screens and gravel.

When the groundwater level in the monitoring well 110 decreases to a predetermined height, the extracting flow rate can suddenly decrease to a relatively small value. At the moment of the sudden decrease of the extracting flow rate, groundwater still inertially flows into the monitoring well 110 at a relatively large speed, which is greater than the extracting flow rate, to induce a rise of the groundwater level in the monitoring well 110. In addition, groundwater pumped out by the water suction pump 112 at this time period was freshly flowed into the monitoring well 110, so is more representative to the groundwater quality of the around area. Therefore, the representative groundwater can be efficiently sampled in a relatively short time.

Figure 2:
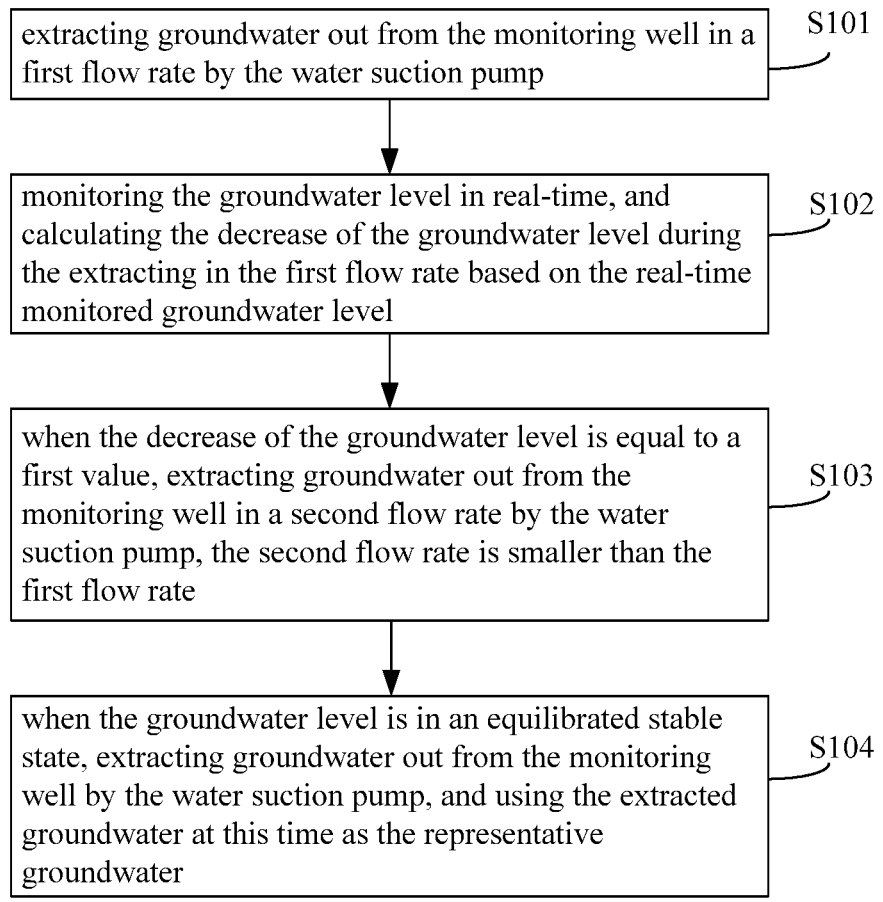
FIG. 2 is a flowchart of an embodiment of a method for sampling groundwater.

Referring to FIG. 2, an embodiment of a method for sampling representative groundwater includes the following steps:

S101, extracting groundwater out from the monitoring well 110 at a first flow rate by the water suction pump 112;

S102, monitoring the groundwater level in real-time, and calculating the decrease of the groundwater level during the extracting at the first flow rate based on the real-time monitored groundwater level;

S103, when the decrease of the groundwater level is equal to a first value, extracting groundwater out from the monitoring well 110 at a second flow rate by the water suction pump 112, the second flow rate being smaller than the first flow rate; and S104, when the groundwater level is in an equilibrated stable state, extracting groundwater out from the monitoring well 110 by the water suction pump 112, and using the extracted groundwater at this time as the representative groundwater.

In an embodiment, the groundwater sampling system can include at least one water suction pump 112 to extract groundwater at the same first flow rate from a plurality of monitoring wells 110 in the same area one after another. Optionally, the diameter and/or depth of different monitoring wells 110 can be the same or different. An inner diameter of the monitoring well 110 can be in a range from about 5 centimeters (cm) to about 10 cm. The hydraulic conductivity of soil around different monitoring wells 110 can be the same or different. Hydraulic conductivity is a property that describes the ability of groundwater to pass through the pores of soil around the monitoring well 110. The speed of groundwater entering the monitoring well 110 is related to the hydraulic conductivity and the extracting flow rate. The greater the hydraulic conductivity of soil around the monitoring well 110, the easier the groundwater enters the monitoring well 110 of groundwater, the faster the groundwater enters the monitoring well 110, and vice versa. The larger the extracting flow rate, the faster the groundwater enters the monitoring well 110, and vice versa.

During the extracting of groundwater out from the monitoring well 110 at the first flow rate, the groundwater level continuously decreases. In S102, the groundwater level in the monitoring well 110 can be measured or sensed in real-time by using the water level indicator 111. Accordingly, the decrease $\Delta h_1$ of the groundwater level in the monitoring well 110 during the extracting out at the first flow rate can be calculated in real-time, by subtracting the current groundwater level $H_2$ from the original groundwater level $H_1$ before the extraction; that is, $\Delta h_1 = H_1 - H_2$. The calculated value $\Delta h_1$ is the first value. $H_1$ is the groundwater level before the extracting at the first flow rate. $H_2$ is the current groundwater level in real-time.

In S103, when the groundwater level is decreased for the predetermined first value, the extracting flow rate can suddenly decrease from the first flow rate to the second flow rate. In an embodiment, the first flow rate is proportional to the second flow rate. In an embodiment, the second flow rate can be in a range from about 0.3 L/min to 0.6 L/min. The first flow rate can be 5 to 10 times of the second flow rate. The second flow rate can be decided according to the diameter of the monitoring well 110 and the hydraulic conductivity of soil around different monitoring wells 110.

In S104, at the moment of the sudden decrease of the extracting flow rate, groundwater still inertially enters into the monitoring well 110 at a relatively large speed, which is greater than the decreased extracting flow rate (e.g., the second flow rate), to induce a rise of the groundwater level in the monitoring well 110. After that, as the water suction pump 112 keeps extracting groundwater from the monitoring well 100 at the second flow rate, the speed of groundwater entering the monitoring well 110 continuously decreases, and the rising speed of the groundwater level continuously decreases. The speed of groundwater entering the monitoring well 100 is then decreased to the value equal to the extracting flow rate (e.g., the second flow rate), so that in the monitoring well 100, the entering of groundwater is to be equilibrated with the extracting out of groundwater, and the groundwater level reaches the relatively stable state.

It is to be understood that, after extracting groundwater out for a period of time, the entering of groundwater is equilibrated with the extracting out of groundwater; that is, the speed of groundwater entering the monitoring well 110 is equal to the extracting flow rate in the equilibration state. The greater the hydraulic conductivity of soil around the monitoring well 110, the faster the system reaches the equilibration state.

When the groundwater level is stable in the equilibration state, groundwater extracted out from the monitoring well 110 can be used as the representative groundwater. It can be understood that, the groundwater level in the equilibration state can be static or have relatively small change. The representative groundwater is a water sample that can be used for accurately analyzing the groundwater quality around the monitoring well 110. The analysis results of the representative groundwater can be used to control groundwater pollution.

The groundwater sampling method provided in this embodiment adopts the water suction pump 112 to extract groundwater from the monitoring well 110 at the first flow rate, obtains the groundwater level in real-time, and calculates the decrease of the groundwater level during the extraction of groundwater at the first flow rate. When the groundwater level decreases for the predetermined first value, the extracting flow rate is decreased to the second flow rate until the groundwater level is in the equilibrium state. The groundwater extracted in the equilibrium state is used as the representative groundwater sample. The method can extract representative groundwater from the monitoring well in a relatively short time by changing the extracting flow rate. Therefore, the representative groundwater can be efficiently sampled in a relatively short time. In addition, the method is applicable to different soil conditions, and it is not necessary to evaluate the soil condition in advance, which also improves the sampling efficiency. The sampling system used in this method is simple, easy to operate, and cost-efficient.

Figure 3:
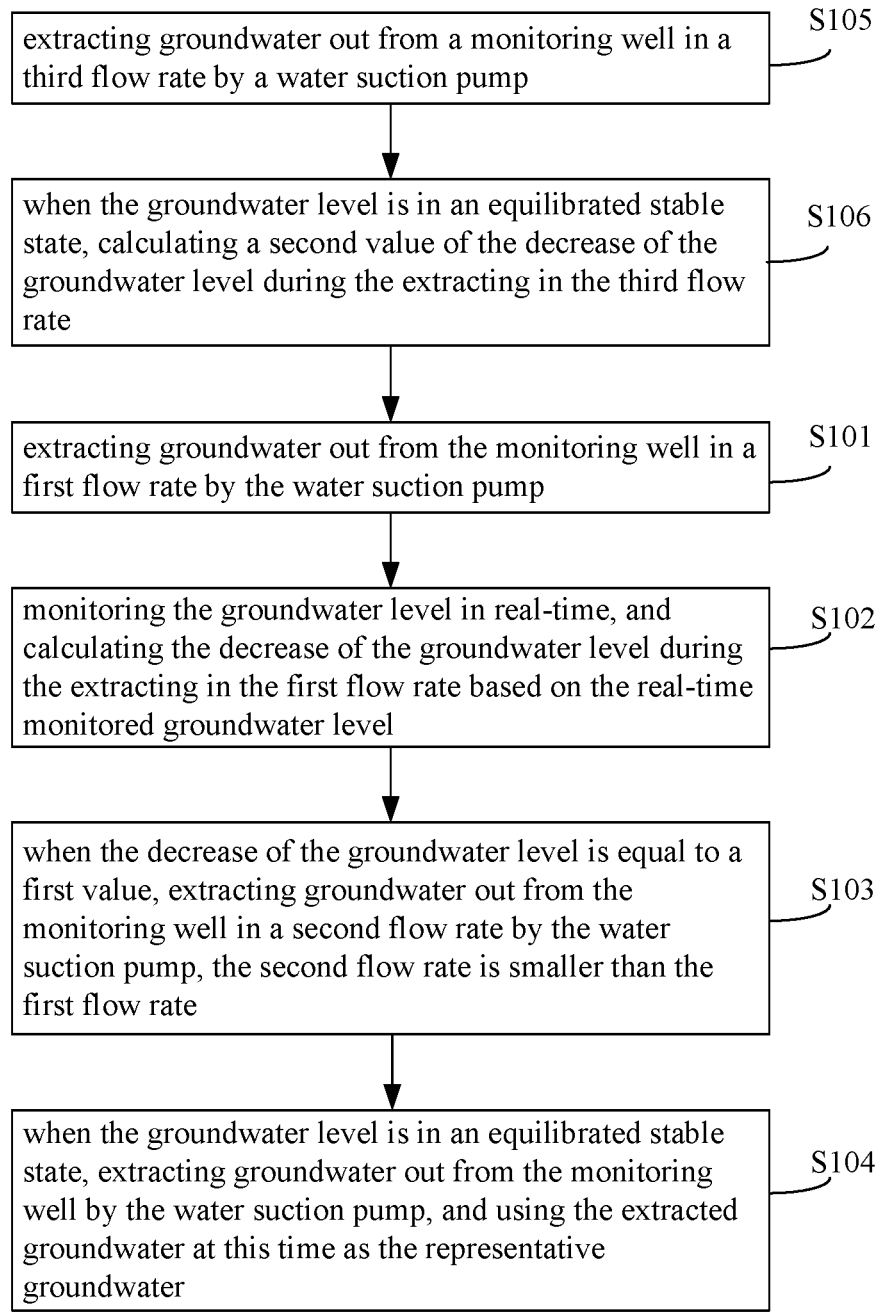
FIG. 3 is a flowchart of another embodiment of the method for sampling groundwater.

Referring to FIG. 3, in an embodiment, before the step S101, the method further includes:

S105, extracting groundwater out from the monitoring well 110 at a third flow rate by the water suction pump 112, the third flow rate being equal to the second flow rate; and S106, when the groundwater level is in an equilibrated stable state, calculating the decrease, as a second value, of the groundwater level during the extracting at the third flow rate.

In an embodiment, there are a plurality of monitoring wells 110 in the same area to be monitored, steps S105 and S106 can be applied to just one monitoring well 110 to determine the second value for all monitoring wells 110. The second value is measured to determine the first value used in S103.

In an embodiment, the first value is proportional to the second value. In a more specific embodiment, the first value is 3 to 4 times of the second value.

By performing S105 and S106, the first value used in S103 is thereby decided according to the conditions of the monitoring well 110. The third flow rate in S105 is also used as the second flow rate in S103. Accordingly, in an embodiment, before the step S101, the method further includes a step S107 for previously determining the first value, including: S107, determining the first value according to the second value, wherein the first value is set to be proportional to the second value, and in an embodiment, is 3 to 4 times of the second value.

S106 is similar to S104. After extracting groundwater out for a period of time, the entering of groundwater will be equilibrated with the extracting out of groundwater; the speed of groundwater entering the monitoring well 100 will be equal to the extracting flow rate (e.g., the third flow rate). The decrease $\Delta h_2$ of the groundwater level in the monitoring well 110 during the extracting out at the third flow rate can be calculated, by subtracting the groundwater level $H_3$ in the equilibration state from the original groundwater level $H_0$ before the extracting out; that is, $\Delta h_2 = H_0 - H_3$. The calculated value of $\Delta h_2$ is the second value. $H_3$ is the groundwater level in the equilibration state during extracting groundwater out at the third flow rate. $H_0$ is the original groundwater level before the extracting at the third flow rate.

In most of the situations and embodiments, $H_0$ is equal to $H_1$, and is a natural level of groundwater in the same or different monitoring wells 110 in the same area to be monitored before any extracting step. It is to be noted that S105 to S107 are optional steps for determining the first value, and the two monitoring wells in S101-S104 and S105-S107 are not needed to be the same one.

In another embodiment, when the groundwater level is in the equilibration state after extracting at the third flow rate for a period of time, the extracting flow rate of the water suction pump 112 can be directly and suddenly changed from the third flow rate to the first flow rate, to directly perform the steps S101 to S104. Therefore, in this embodiment, $H_3$ is equal to $H_1$, which is not only the groundwater level in the equilibration state during the extracting at the third flow rate, but also the starting point of the decrease $\Delta h_1$ of the groundwater level during the extracting at the first flow rate.

In some embodiments, the second value is in a range from about 0.2 meters (m) to about 0.4 m. The first value can be 3 to 4 times of the second value.

In the embodiments of the method for sampling representative groundwater, the second value $\Delta h_2$ is the height decrease of groundwater level during the extracting at the third flow rate from the original groundwater level to the equilibrated level. By obtaining the second value $\Delta h_2$, the first value $\Delta h_1$ can be determined accordingly and used in the following steps of extracting at the first flow rate. For example, $\Delta h_1$ can be set to 3 to 4 times of $\Delta h_2$.

The embodiment of the method for sampling groundwater extracts groundwater from the monitoring well 110 at the third flow rate to previously obtain $\Delta h_2$. Thereby, the second flow rate can be determined according to the third flow rate, and the first value can be determined according to the second value. The groundwater extracted in the equilibrium state is used as the representative groundwater sample. The method can extract representative groundwater from the monitoring well in a relatively short time by changing the extracting flow rate. Therefore, the representative groundwater can be efficiently sampled in a relatively short time. In addition, the method is applicable to different soil conditions, and it is not necessary to evaluate the soil condition in advance, which also improves the sampling efficiency. The sampling system used in this method is simple, easy to operate, and cost-efficient.

The technical features of the above-described embodiments may be arbitrarily combined. In order to make the description simple, not all possible combinations of the technical features in the above embodiments are described. However, as long as there is no contradiction in the combination of these technical features, the combinations should be in the scope of the present disclosure.

What described above are only several implementations of the present disclosure, and these embodiments are specific and detailed, but not intended to limit the scope of the present disclosure. It should be understood by the skilled in the art that various modifications and improvements can be made without departing from the conception of the present disclosure, and all fall within the protection scope of the present disclosure. Therefore, the patent protection scope of the present disclosure is defined by the appended claims

What is claimed is:

1. A method for sampling groundwater, the method comprising:

extracting groundwater from a monitoring well at a first flow rate;

monitoring groundwater level in real-time, and calculating a decrease of the groundwater level during the extracting at the first flow rate based on the real-time monitored groundwater level;

when the decrease of the groundwater level is equal to a first value, extracting groundwater from the monitoring well at a second flow rate, the second flow rate being smaller than the first flow rate; and when the groundwater level is in an equilibration state, extracting groundwater from the monitoring well and using the extracted groundwater at this time as a representative groundwater;

before the extracting groundwater from the monitoring well at the first flow rate, the method further comprising:

Extracting groundwater from the monitoring well at a third flow rate, the third flow rate being equal to the second flow rate; and when the groundwater level is in another equilibration state, obtaining a second value of the decrease of the groundwater level during the extracting at the third flow rate.

2. The method of claim 1, wherein the extracting groundwater from the monitoring well at the third flow rate comprises:
 extracting groundwater from one of a plurality of monitoring wells in the same area to be monitored.

3. The method of claim 1, before the extracting groundwater from the monitoring well at the first flow rate, further comprising:
 determining the first value according to the second value by setting the first value being proportional to the second value.

4. The method of claim 3, wherein the first value is 3 to 4 times of the second value.

5. The method of claim 1, wherein the second value is in a range from about 0.2 meters to about 0.4 meters.

6. The method of claim 1, wherein groundwater is extracted from the monitoring well by a water suction pump.

7. The method of claim 1, wherein the groundwater level is monitored by a water level indicator.

8. The method of claim 1, wherein the first flow rate is proportional to the second flow rate.

9. The method of claim 1, wherein the first flow rate is 5 to 10 times of the second flow rate.

10. The method of claim 1, wherein the second flow rate is in a range from about 0.3 L/min to 0.6 L/min.

11. The method of claim 1, wherein an inner diameter of the monitoring well is in a range from about 5 cm to about 10 cm.

\* \* \* \* \*